(12) United States Patent
Yule et al.

(10) Patent No.: US 8,823,519 B2
(45) Date of Patent: Sep. 2, 2014

(54) PASTURE MANAGEMENT

(75) Inventors: Ian Yule, Palmerston North (NZ); Robert Murray, Palmerston North (NZ); Hayden Lawrence, Hawera (NZ); James Frederick Stewart, Palmerston North (NZ); Willem-Peter Vander Laan, Masterton (NZ)

(73) Assignees: C-Dax Limited, Christchurch (NZ); Massey University, Palmerston North (NZ)

(*) Notice: Subject to any disclaimer, the term of this patent is extended or adjusted under 35 U.S.C. 154(b) by 1858 days.

(21) Appl. No.: 11/917,144

(22) PCT Filed: Jun. 8, 2006

(86) PCT No.: PCT/NZ2006/000142
§ 371 (c)(1),
(2), (4) Date: Jun. 17, 2010

(87) PCT Pub. No.: WO2006/132549
PCT Pub. Date: Dec. 14, 2006

(65) Prior Publication Data
US 2010/0283603 A1    Nov. 11, 2010

(30) Foreign Application Priority Data
Jun. 8, 2005 (NZ) ........................................ 540613

(51) Int. Cl.
| G08B 21/00 | (2006.01) |
| G01B 11/14 | (2006.01) |
| G01B 11/02 | (2006.01) |
| G01S 17/87 | (2006.01) |
| A01B 79/00 | (2006.01) |
| G01S 17/08 | (2006.01) |
| G01S 17/88 | (2006.01) |

(52) U.S. Cl.
CPC ............... *A01B 79/005* (2013.01); *G01S 17/87* (2013.01); *G01S 17/08* (2013.01); *G01S 17/88* (2013.01)
USPC ........... 340/540; 356/625; 356/634; 356/638; 702/1; 702/19; 702/127

(58) Field of Classification Search
USPC ................ 340/540; 356/625–640; 250/336.1, 250/338.1, 221, 222.1, 559.19, 559.22, 250/559.26, 559.12, 559.13, 559.15; 702/1, 702/19, 127, 188
See application file for complete search history.

(56) References Cited

U.S. PATENT DOCUMENTS 3,672,775 A * 6/1972 Fruengel ........................ 356/343
4,197,694 A   4/1980 Hagie et al.
(Continued)

FOREIGN PATENT DOCUMENTS

| DE | 100 02 880 | 6/2001 |
| DE | 103 49 324 | 5/2005 |

(Continued)

OTHER PUBLICATIONS http://www.nal.usda.gov/ttic/tektran/data/000008/2500000082542.html. "Holes in Precision Farming: Mechanistic Crop Models." 1998.

(Continued)

*Primary Examiner* — Daniel Wu
*Assistant Examiner* — Kam Ma
(74) *Attorney, Agent, or Firm* — Merchant & Gould P.C.

(57) ABSTRACT

Systems, methods, and apparatuses for gathering data are disclosed. For example, a plant matter sensor includes a pair of parallel spaced apart sensor arms and a control console, a first of the arms having a plurality of emitter spaced along its length, each emitter configured to emit a signal substantially perpendicularly to the arm to be received by a corresponding receiver on the second arm. The console contains controller means to control the rate, strength and regularity of the signal emitted by each of the emitters, collectors to collect data from each receiver as to the existence or absence of receipt of a signal, a processor to process data received from the controllers and the collectors and determine the height of any plant matter traversed by the plant matter sensor and predetermined intervals, and storage to store the plant matter height data generated by the processor for subsequent download or analysis.

21 Claims, 6 Drawing Sheets

(56) References Cited

U.S. PATENT DOCUMENTS

| | | | |
|---|---|---|---|
| 5,279,157 A * | 1/1994 | Mattis et al. ............... 73/290 R |
| 5,793,035 A * | 8/1998 | Beck et al. ................ 250/222.1 |
| 5,837,997 A | 11/1998 | Beck et al. |
| 5,842,307 A * | 12/1998 | May ................................ 47/1.7 |
| 6,021,602 A * | 2/2000 | Orsi ............................... 47/62 A |
| 6,055,702 A * | 5/2000 | Imamura et al. ................ 15/339 |
| 6,137,577 A * | 10/2000 | Woodworth ................... 356/623 |
| 6,181,095 B1* | 1/2001 | Telmet ........................... 318/480 |
| 6,282,967 B1 | 9/2001 | Homburg et al. |
| 6,345,231 B2* | 2/2002 | Quincke ........................ 701/468 |
| 6,374,584 B1* | 4/2002 | Blanchard ........................... 56/1 |
| 6,393,927 B1* | 5/2002 | Biggs et al. ..................... 73/866 |
| 6,401,549 B1* | 6/2002 | Ohlemeyer .................. 73/861.73 |
| 6,414,603 B1* | 7/2002 | Yamaguchi et al. ....... 340/815.4 |
| 6,596,996 B1 | 7/2003 | Stone et al. |
| 6,937,939 B1* | 8/2005 | Shibusawa et al. ............. 702/22 |
| 7,081,611 B2* | 7/2006 | Scott ............................. 250/221 |
| 7,412,330 B2* | 8/2008 | Spicer et al. ...................... 702/2 |
| 7,472,437 B2* | 1/2009 | Riley et al. ........................ 5/600 |
| 2002/0014116 A1 | 2/2002 | Campbell et al. |
| 2003/0004630 A1 | 1/2003 | Beck |
| 2005/0024213 A1 | 2/2005 | Franzen et al. |
| 2006/0145101 A1* | 7/2006 | De Coi ...................... 250/559.12 |
| 2009/0281733 A1* | 11/2009 | Yamamoto et al. ............. 702/19 |
| 2010/0088032 A1* | 4/2010 | Nielsen et al. .................... 702/5 |
| 2010/0179767 A1* | 7/2010 | Goldman et al. ................ 702/19 |
| 2010/0283603 A1* | 11/2010 | Yule et al. ..................... 340/540 |

FOREIGN PATENT DOCUMENTS

| | | |
|---|---|---|
| DE | 10349324 A1 * | 5/2005 |
| EP | 1 493 316 | 1/2005 |
| GB | 2 044 064 | 10/1980 |
| JP | 2002 101770 | 4/2002 |
| WO | WO 01/61617 | 8/2001 |
| WO | WO 2006/009472 | 1/2006 |

OTHER PUBLICATIONS http://lubbock.tamu.edu/ipm/AgWeb/r_and_d/cotton/1998/sidr-rootnot.html. "Use of Corn Cover Crop as a Bioindicator of Root-Knot Nematode in Cotton." 1998.

Silsoe College Thesis—Mark Moore—"An investigation into the accuracy of yield maps and their subsequence use in crop management." 1998.

http://txprecag.tamu.edu/content/res/hs.htm. "Crop Height and Plant Population Sensor." retrieved Dec. 17, 2007.

European Search Report for Application No. 06 76 9466 dated Dec. 6, 2012.

Dzinaj et al. "Multi-sensor-System for distinguishing between crops and weeds." *Zeitschrift fur Pflanzenkrankheiten und Pflanzenschutz.* Jan. 1, 1998. pp. 233-242. (English Translation provided).

Fender et al. "Messende Lichtgitter und Multispektralkameras als bildgebende Systeme zur Pflanzenerkennug." *Bornimer Agrartechnische Berichte.* May 10, 2005. pp. 7-16. (English abstract provided).

Rayburn et al. "Estimating Pasture Forage Mass From Pasture Height." http://www.wvu.edu/-agexten/forglvst/passmass.pdf. Oct. 1, 2003.

Ruckelshausen et al. "Microcontroller-based multi-sensor system for online crop/weed detection." *Proceedings 1999 Brighton Conference.* Jan. 1, 1999. pp. 601-606.

\* cited by examiner

PASTURE MANAGEMENT

FIELD OF THE INVENTION

This invention relates to pasture management, and more particularly to a system for pasture management and to hardware and software components of such a system.

BACKGROUND ART

It is generally recognised by commentators and researchers that the next significant frontier in agriculture is the formulation and application of precision agricultural techniques. Precision agriculture means the collection of site-specific information, application of that site-specific information in site-specific analysis, and the subsequent making of decisions in truly site-specific manner.

Fundamental to the philosophy of precision agriculture is the concept of matching site-specific inputs to site-specific needs; if a part of a field needs more fertilizer, give that part more fertilizer; if a section of a crop needs harvesting early, harvest it early. These are simple, common-sense ideas. However, like many good ideas, there is a significant gap between theory and implementation. The use of management zones is currently the most practical way to implement the theory of precision agriculture. However, this is not truly precision agriculture, as the size of the zones and the process of data collection necessarily involves a relatively significant degree of averaging which in turn impacts on how site-specific decision making can be.

One critical area ripe for application of precision agriculture techniques is in feed budgeting systems. Dairy commentators and researchers have suggested that by the use of such systems a net improvement in pasture utilisation of between 10-15% may be possible. Using current production costs and returns, including costs associated with increased stocking rate as at the present date estimates, indications are that for New Zealand in 2005 NZ$ terms a 10% improvement correlates to an improvement of some $559 million, with a 15% improvement correlating to an $871 million increase.

The gains are based on assumptions that a number of contributing factors will align. One of the more obvious primary contributors is the fact that farmers would be in a position to develop a budgeting approach and make better decisions regarding feed, production and use, but there are other short and long term benefits.

Short term benefits include being able to more accurately place break fences and in the calculation of the amount of supplementary feed required, which would mean that cows are less likely to be underfed, which is detrimental to production, or overfed, which is wasteful of resources.

Longer term benefits centre around the ability to identify areas or zones within a paddock that are less productive than others, or have less palatable grass. This means that application of fertilisers, weed sprays, drainage, irrigation, over sowing of pasture etc could be targeted at those particular zones.

One of the main problems with being able to implement a system of precision pasture management relates to the difficulty of securing an adequate method of pasture measurement. More specific problems include difficulties with obtaining accurate individual measurements or samples, and with obtaining sufficient samples that will allow variability to be taken into account.

One of the more common methods of pasture measurement today involves the use of a rising plate meter. There is little intrinsically wrong with rising plate meter measurements as a means of pasture measurement. The problem is that they are slow to use, and so take considerable time to provide enough samples to form an accurate picture of production, and because fewer readings are inherently taken considerable care must be employed to make sure that any readings which are taken are truly representative of the paddock being measured.

Fewer samples also give rise to significant potential for errors to creep in, and for any errors to become amplified in their impact.

A typical error is of the kind generated when the point of measurement is not representative of the paddock—a particular problem with pasture which is heavily pugged conditions—for example, depending on the total number of readings taken, a reading from the base of a 75 mm hoof print could theoretically have the effect of erroneously adding 920 kg of dry matter to the plate reading (Assuming 120 kgD-Mha-1 per cm of plate height). Operator error is thus a significant contributing factor.

Errors become more important when measuring growth rates, the shorter the time interval between measurements the worse the problem and the more important is the repeatability of measurement.

Further, because of the time consuming nature of doing a pasture cover analysis using a rising plate meter, they are typically done at best every 10 days or so. As a result only a "snapshot" in time of pasture cover is measured. However, such a "snapshot" allows a feed wedge to be determined from the data derived which can indicate an upcoming feed surplus or shortage in the next few weeks.

What is not practically possible with a rising plate meter because of the time taken to complete, but which would be extremely beneficial, is a set of pasture pre-grazing measurements taken just before grazing a paddock, and a second set just after grazing a paddock to establish the residual pasture cover, thereby allowing total grass grown between grazings to be calculated, along with the average kilograms of dry matter consumed by each animal to be derived after the fact.

There is clearly a need for an improved method and means for pasture measurement to realise the significant benefits that precision pasture management offers, and it is an object of the present invention to provide such an improved method and means, and consequently an improved method and system of pasture management, or at least to provide the public with a useful choice.

SUMMARY OF THE INVENTION

In a first broad aspect this invention provides a plant matter sensor, the sensor comprising a pair of parallel spaced apart sensor arms and a control console, a first of said arms having a plurality of emitter means spaced along its length, each emitter means configured and arranged to, in use, emit a signal substantially perpendicularly to the said arm to be received by a corresponding receiver means on the second arm, the console containing control means to, in use, control the rate, strength and regularity of the signal emitted by each of the said emitter means, collection means to, in use, collect data from each receiver means as to the existence or absence of receipt of a signal, processor means to process data received from the control means and the collection means and determine the height of any plant matter traversed by the plant matter sensor and predetermined intervals, and storage means to store the plant matter height data generated by the processor means for subsequent download or analysis.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components which it directly references, but also to other non-specified components or elements. This rationale will also be used when the term 'comprised' or 'comprising' is used in relation to one or more steps in a method or process.

Preferably the sensor arms are disposed substantially vertically.

Desirably the sensor emitter means are optimised to emit, and said receiver means are optimised to receive, light in the infra-red spectrum.

Optimally the sensor includes twelve emitter means paired with twelve receiver means.

Conveniently the emitter means and corresponding receiver means are spaced at 20 mm intervals along the sensor arms.

Advantageously the emitter means operate as four banks of three, with every fourth emitter means along the length of the first sensor arm being part of the same bank.

Desirably each bank of emitter means emits a pulse of infra-red light in series, preferably with each bank emitting a pulse of no more than 100 milliseconds long.

Preferably the sensor is adapted to be able to take at least 200 readings per second.

Optimally the emitter means emit a high intensity pulse of infra-red light utilising a high current to do so, preferably at least 250 mA.

Desirably the processor means monitors the receiver means for faults, so that if a potential fault is detected the console is able to provide an alert to the operator.

Preferably the plant matter sensor further includes a GPS receiver such that, in use, each set of data collected by the collection means is geo-referenced as to its collection position.

Preferably the sensor is configured and arranged as a pasture sensor.

Advantageously the sensor processor means converts height readings to pasture density as kilograms of dry matter per hectare.

Desirably the console further includes display means.

Preferably the sensor further includes a user input interface to enable an operator to input the appropriate time of year and pasture type so that the processor uses the appropriate conversion calculations when calculating pasture density.

Optionally the number of emitter means and the sensor reading rate is sufficient to generate a constant silhouette of the plant matter along the line of sensor travel.

Desirably the processor means is able to automatically determine the pasture type based on real-time analysis of silhouette by the processor means. Conveniently real-time analysis of the silhouette is also able to identify different plant parts and presence and type of any weeds.

Preferably the processor means is adapted to determine in real-time an appropriate metabolised energy value for each particular plant in the silhouette on the basis of recognition via the silhouette.

Preferably the sensor further includes wireless data transfer means to wirelessly upload and download data.

In a second broad aspect this invention provides a support frame for the plant matter sensor of the first broad aspect, the frame comprising attachment means for attaching the support frame to a towing vehicle, sensor mounting means for mounting a plant matter sensor of the first broad aspect and maintain it in a substantially vertical orientation, and ground engagement means to maintain a said plant matter sensor at a predetermined level above the ground during operation.

Preferably the support frame is configured and arranged to be towed behind a towing vehicle.

Desirably the ground engagement means comprise a pair of parallel spaced apart skids.

Advantageously the support frame further includes wheels for transporting the sensor from one location to another while not in use such that the ground engagement means are no long in ground engagement.

Desirably the transport wheels are adapted to move from a transport position to a second position whereat the ground engagement means are in ground engagement and said transport wheels serve as stabilizers against the support frame tipping over sideways, when in use.

Preferably the ground engagement skids each further include a downwardly projecting blade running substantially the length of the underside of the skid.

Conveniently the support frame further includes a mounting means to enable the support frame to be attached to a towing vehicle.

Desirably the support frame further includes a pair of spaced apart deflector guards configured and arranged to, in use, present a defined bandwidth of pasture passing between the sensor arms. Advantageously the defined bandwidth of pasture is 20-200 millimeters narrower than space between sensor arms.

In a third broad aspect this invention provides a sensor assembly comprising a sensor of the first broad aspect above mounted in the support frame of the second broad aspect above.

Preferably the sensor assembly is sufficiently heavy that with the ground engagement means of the support frame comprising skids, in use, the ground beneath the skids is slightly flattened as the skids pass over thereby achieving a smoother ride.

Desirably the sensor assembly is adapted to travel at a rate of 15-25 kph.

In a fourth broad aspect this invention provides a suite of computer software for receiving data from a pasture sensor according to the first broad aspect, said suite including a data input module to enable data stored in the storage means of the pasture sensor to be input into the suite for subsequent analysis, a pasture cover module to analyse and record pasture cover over one or more paddocks, and to generate a feed availability report on a paddock by paddock basis, and display an associated feed wedge and, using historical comparative data from earlier pasture sensor readings, together with predetermined seasonal information, pasture type information, and weather information, forecast future feed availability.

Preferably, where the data available from the pasture sensor is geo-referenced, the software suite further includes a mapping module enabling the path followed by the pasture sensor during the reading process to be displayed on a map of the paddock assessed so as to enable a determination to be made of the reading accuracy.

Desirably the mapping module can also generate a contoured map of the paddock assessed to show variations in the feed availability within the paddock.

Advantageously the suite is adapted to determine the position of paddock temporary fence breaks for feed control.

Preferably the mapping module uses the Kriging algorithm to display pasture contour/profile information based on geo-referenced pasture density readings.

Advantageously the suite is operable on a personal computer, with lesser functionality operable directly on a PDA.

Desirably data generated by the suite can be uploaded to the PDA for use in the field.

Preferably the PDA is able to receive data wirelessly from the pasture sensor console and display the data received on a relevant paddock map to show a geo-referenced readings trail to enable assessment of the acceptability of the sensing progress, and in particular to identify any areas in which insufficient readings may have been taken.

Conveniently the suite is able to analyse successive pasture sensor readings over time and assess specific areas for which data is provided to determine those areas requiring targeted fertiliser application, weed spraying, pasture renewal, irrigation, and/or drainage to improve pasture yield.

Preferably the suite is able to output in electronic form a map showing areas requiring targeted fertiliser application, irrigation, and/or drainage for use by contractors such as fertiliser applicators, irrigation contractors and the like.

In a fifth broad aspect this invention provides a method of pasture management using the sensor of the first broad aspect above in conjunction with the software of the third broad aspect above, the method comprising the steps of:
 a. Undertaking an initial assessment of the feed availability in one or more paddocks using the pasture sensor of the first broad aspect to secure geo-referenced pasture cover data;
 b. Uploading the geo-referenced pasture cover data from the pasture sensor to the software of the fourth broad aspect above, and determining feed availability variations within each paddock; and
 c. Referencing the feed availability variations within a paddock optimise the location or locations for break fencing so as to ensure optimised feed availability within the break fenced area as necessary for the number of animals and production considerations applicable.

Preferably the method further includes the steps of uploading the paddock and break fence location data to a PDA to enable the break fencing locations to be established and verified in the field.

Desirably the method further includes the steps of taking subsequent geo-referenced pasture cover readings for the same paddocks after a predetermined time period for subsequent use as indicated in steps b and c, and additionally for comparative assessment with the initial and any subsequent geo-referenced data sets for the same paddock to enable changes in pasture cover to be monitored at any position within the said paddock thereby facilitating location specific decisions to be made as to fertiliser application, watering, drainage, and over sowing, as well as the monitoring and re-assessment of the impact of those decisions to be undertaken.

Preferably the method further includes the step of a PDA receiving data wirelessly from the pasture sensor console and display the data received on a relevant paddock map to show a geo-referenced readings trail to enable assessment of the acceptability of the sensing progress, and in particular to identify any areas in which insufficient readings may have been taken.

Conveniently the method further includes the step of outputting in electronic form a map showing areas requiring targeted fertiliser application, irrigation, and/or drainage for use by contractors such as fertiliser applicators, irrigation contractors and the like.

BRIEF DESCRIPTION OF THE DRAWINGS

The invention is further described by way of example with reference to preferred embodiments of the various aspects thereof. The accompanying drawings illustrate the invention by way of example only and are not intending to limit its scope. In the drawings.

DETAILED DESCRIPTION OF THE INVENTION

Figure 5:
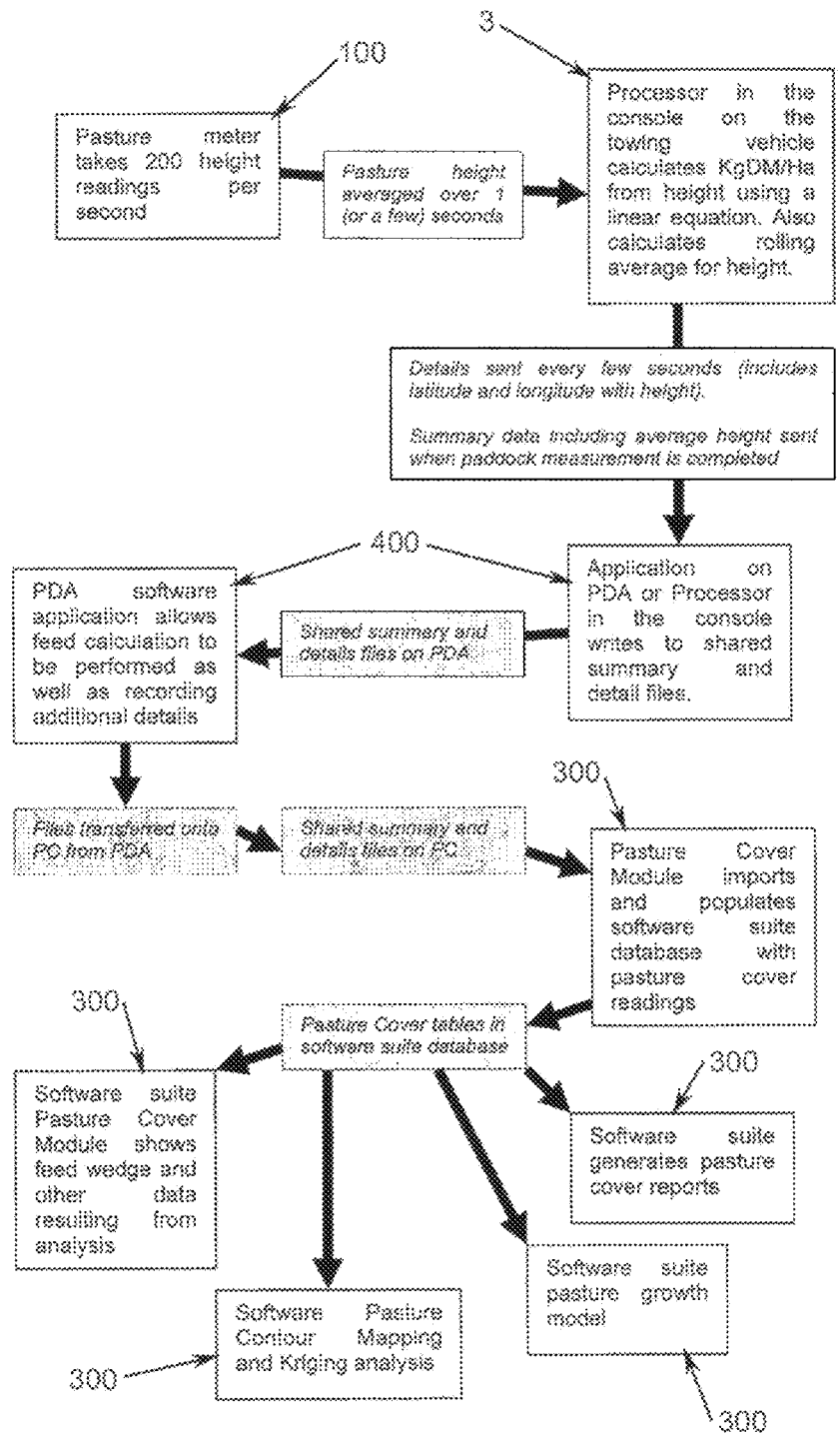
FIG. 5: shows a schematic diagram of the data flow following a preferred embodiment of the method of the present invention.
Figure 6:
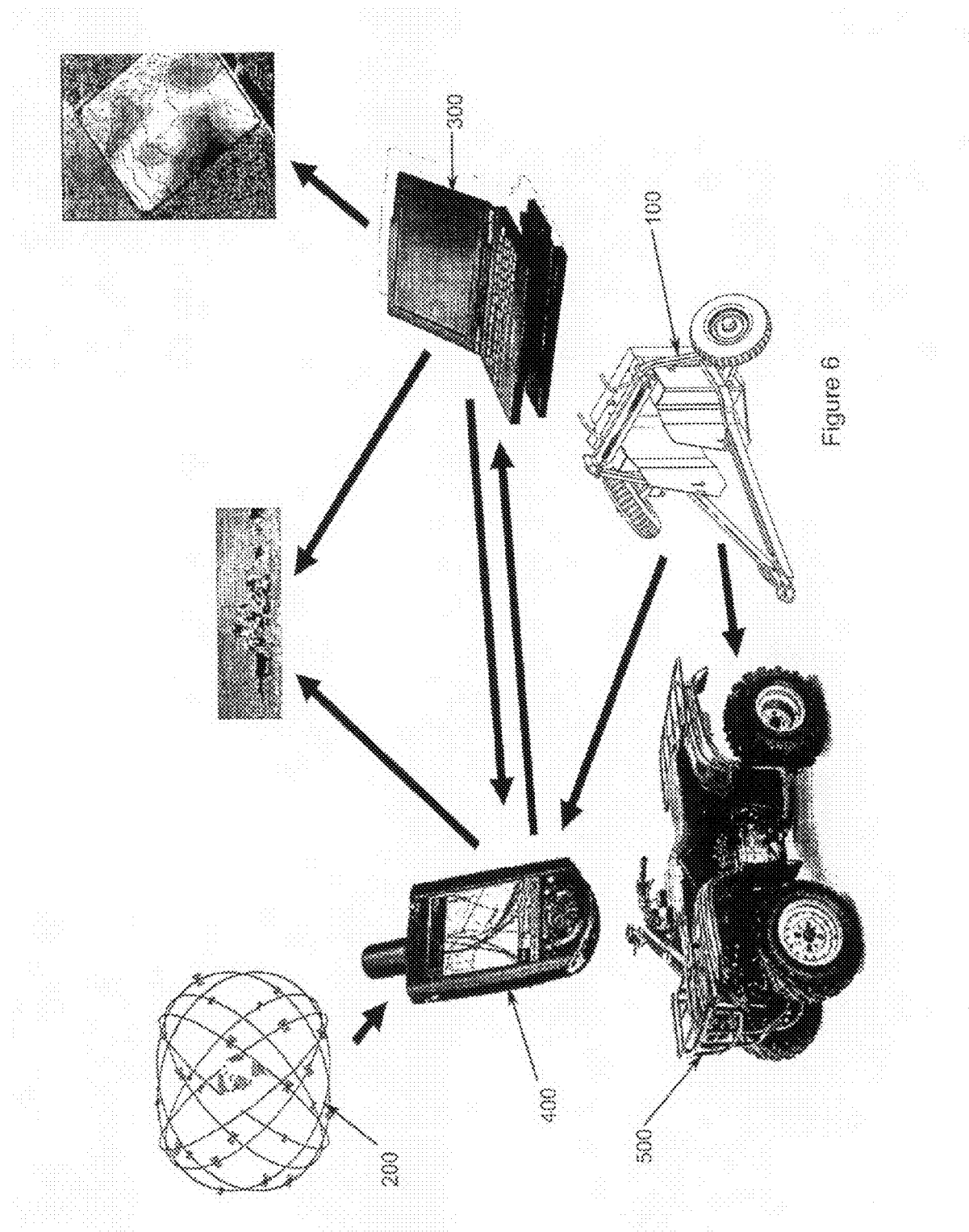
FIG. 6: shows a schematic overview of the components of the pasture management system and method of the present invention.

Referring to the drawings, and in particular to FIGS. 1 to 4, the pasture meter of the present invention is generally indicated at 100, and comprises two major parts, the sensor arms 2 which are mounted on a towing frame 1, and control and display console (illustrated schematically in FIG. 5 at 3) which is mounted on the towing vehicle, such as, for example, the ATV shown as 500 in FIG. 6.

As can be seen, the sensor arms 2 are set in parallel, space apart, relationship, and are mounted on the towing frame 1 so that in use they are maintained in substantially vertical orientation, with their lower ends 4 at or slightly above ground level.

The first, emitter, arm 5 of the sensor arms 2 preferably has twelve infrared LED emitters 6 spaced apart vertically at 20 mm intervals along its length, beginning at the lower end 4. There are twelve corresponding photo transistors 7, optimised for infrared, on the second, receiving, arm 8. The twelve emitters 6 are connected as four banks of three LEDs, so that the first bank, for example, consists of LEDs at positions "1", "5" and "9", the second bank at position "2", "6" and "10", and so on.

Only one bank of emitters 6 is briefly pulsed on at a time, desirably for in the order of one hundred microseconds, and is controlled automatically by the display and control console 3. Pulsing one bank of emitters 6 at a time helps eliminate cross-talk between channels, because an individual photo transistor 7 is only exposed to light from the emitter 6 directly opposite. The three adjacent emitters 6 either side are off.

The actual number of emitters 6 in total and in each bank may vary depending on the level of detail required from each reading pulse, and the height and nature of the pasture cover to be read.

A further benefit of using a very short "on" time for each bank of emitters 6 is that high current can be used safely (about 250 mA, although a higher current is considered preferable), giving a high output of infra-red light. The high light output allows the sensitivity of the photo transistors 7 to be reduced, minimising the impact of the infra-red component of ambient daylight.

The pasture sensor 100 preferably has a number of user-selectable measuring modes, interpreting the output from the twelve photo transistors 7 in slightly different ways. For example, a uniformly dense dairy pasture may require a different approach from a dry sparse pasture with seed heads. It is within the contemplation of the present invention for the measuring mode to be auto selected so as to suit the pasture condition.

Desirably a processor (identified schematically in FIG. 5 as part of the console 3) within the display and control console 3 also monitors the photo transistors 7 for fault conditions. For example, a photo transistor 7 that consistently shows no received signal, when adjacent photo transistors 7 are changing between receiving/not receiving as the pasture meter 100 passes through the pasture, is interpreted as a fault. In such circumstances the display and control console 3 can alert the operator to check the emitters 6 and transistors 7.

Calibration of the pasture meter 100 can be undertaken manually to enable seasonal factors to be taken into account. However, automatic calibration is contemplated by detecting grass quality.

There are a number of options in terms of how the pasture meter 100 can be operated.

The principal focus of the meter 100 is to measure pasture height. To that end, in the first mode of operation in any series of readings the pasture meter 100 records the identity of the middle photo transistor 7 to present a no signal receipt status from the corresponding emitter 6. However, if the no signal receipt status is continuous down the length of the sensor arm 2, or is the status achieved by the middle but not the top photo transistor 7, then that particular reading is recorded as a null reading. Despite that such null readings are accounted for, and can be used as a measure of pasture density or quality. For example, if the pasture contains a large number of seed heads then a high number of null readings would be expected. This would be recorded and can be displayed. However, only full readings are used for pasture quantitative assessment.

In a second mode of operation the pasture meter 100 operates in much the same way as in the first mode described above, however, it is only the top photo transistor 7 which does not receive a signal, and below which all others also do not receive a signal, that is recorded. So for example sensor position "11" has a no signal receipt status reading, but positions "10" and "9" do record a signal receipt, and positions "8" and below are all blocked, the height reading is taken as corresponding to position "8". The advantage of this is that we have a more accurate idea of the actual useful higher quality leafy pasture.

In reality the status of the signal to each of the photo transistors 7 are all continually recorded, with the readings recorded as a 12 digit binary number. Interpretation of that number is a matter for analysis by the pasture meter 100 processor and associated software algorithms and/or firmware.

Optionally the pasture meter 100 can do post-processing of the recorded data to convert a series of height readings into pasture density calibrated as kilograms of dry matter per hectare (kg/DM/Ha). These algorithms are relatively sophisticated, and take into account seasonal variations, long stalky grass where not all sensors are eclipsed contiguously, rough grass where there is a great variation in the height readings, pre and post-grazing situations, pasture species, and disregard occasional interference by contaminants on one or more of the emitters 6 or photo transistors 7.

The pasture meter 100 collects multiple height reads at once, however as described above, the sensor processor averages the height based on the seasonal formula and other operator input values.

By increasing the number of sensors and increasing the reading record rate a far more detailed picture, amounting to a silhouette of the pasture, can be obtained from which it is possible to derive more information. The advantage of having a silhouette which is basically a binary mathematical array of 1's and 0's is that it can be handled and analysed very quickly and efficiently.

Having sufficient data to establish a silhouette of the pasture traversed enables a far greater level of information to be derived about the pasture condition, make up and feed value. Post processing of the gathered data can either take place on the fly as part of the pasture sensor processing functionality, or as part of the software suite.

As illustrated in FIGS. 1 to 4, the preferred embodiment of the frame 1 comprises a mount 11 for the sensor arms 2 of the pasture meter 100, capturing and maintaining them in parallel spaced apart relationship.

Essentially the mount 11 is an inverted U shaped bracket, locating one arm 2 and their associated emitter 6/photo transistor 7 electronic hardware on each "leg" 12 of the U, with the remaining electronics of the sensor arms 2 preferably located safely and securely in the cross portion of the mount 11. Each of the legs 12 terminates in a short skid 13, each preferably having a slightly upturned leading end 14 and flat a trailing end 15.

The under surface 16 of each skid 13 is preferably substantially flat thereby facilitating the sliding of the frame 1 and sensor arm 2 combination over the ground. Desirably extending downwardly from the under surface 16 of each skid 13, parallel to the direction of intended travel of the skid 13, is a blade 17, the purpose of which in use is to minimise lateral sliding of the frame 1 in travel, thereby enhancing the smooth passage of the frame 1 and sensor arms 2 over the ground.

Figure 4:
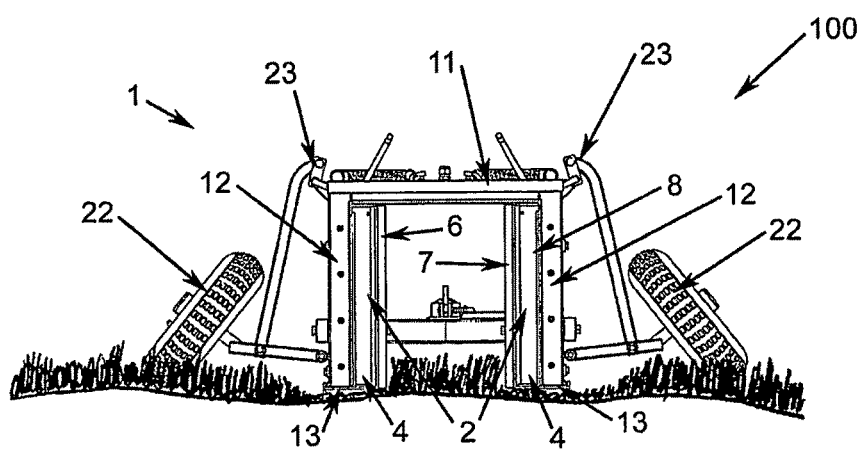
FIG. 4: shows an end elevation of the frame of FIG. 1 with the sensor in the operative position.

The frame 1 further includes attachment means 18 for attaching the support frame 1 to a towing vehicle, such as the ATV 500 of FIG. 4. The attachment means 18 preferably comprises a "V" shaped drawbar 19, having each "leg" of the "V" attaching to a corresponding arm 2 of the sensor 100, and having a tow ball type joint 20 for attachment to a standard tow ball fitted to the towing vehicle.

The weight of the pasture meter 100 assembly, coupled with the trailing arm configuration of the drawbar 19, encourages the skids 13 to maintain ground contact in use. However, with the speed of data measurement at a minimum of 200 cycles per second, which translates into a measurement rate of about one reading per two or three centimeters of ground travel at 15 to 25 kph the loss of a few data sets for a hole or bump is considered to be inconsequential. Holes and similar have the greatest effect on very hard ground, but normal pasture allows for good traverse as the weight of the complete assembly tends to mould the ground as it goes achieving a smoother and more accurate ride.

Other configurations of the frame 1 contemplated include mounting at the front of a vehicle so that it is driven rather than towed, and the use of wheels rather than skids to follow the contours of the paddock being traversed. Longer "skis" as opposed to the shorter skids found in the preferred embodiment are also contemplated. The skids of the preferred embodiment are, however, the preferred ground engagement means.

As can be seen in the drawings of the preferred embodiment, FIGS. 1 to 4, the frame 1 further includes deflector guards 21. The guards 21 are adapted to present a defined bandwidth of pasture between the sensor arms 2. This band width is some 20-200 millimeters narrower than the spacing between the sensor arms 2. The reason for that is to preventing problems with contamination of the glass surfaces covering the emitter 6 and transistor 7 lenses which would otherwise result in erroneous readings and/or failure to detect a signal registration. This can be a particular problem when the grass is damp, wet, or fouled with excrement.

The guards 21 extend substantially from ground level upwards and deflect any animal excrement and other contaminants, as well as grass either transversely outwardly of, or in the case of grass, under, the skids 13 and way from the sensor arms 2.

While the shape and configuration of the guards 21 serve to keep the wet grass and other contaminants from the emitters 6 and transistors 7, other options, such as the use of air pressure to clear the lenses and holes through which the emitters 6 and transistors 7 send and receive is also anticipated.

Figure 1:
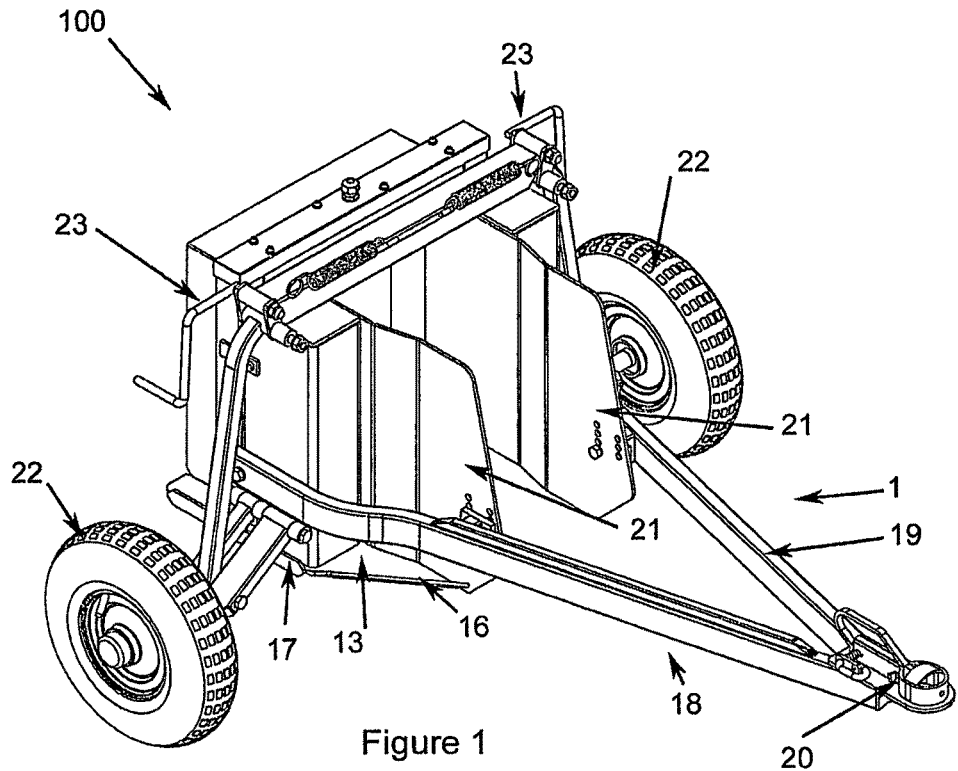
FIG. 1 shows a perspective view of a pasture sensor support frame according to a preferred embodiment of the invention in a non-operational, transport configuration.
Figure 2:
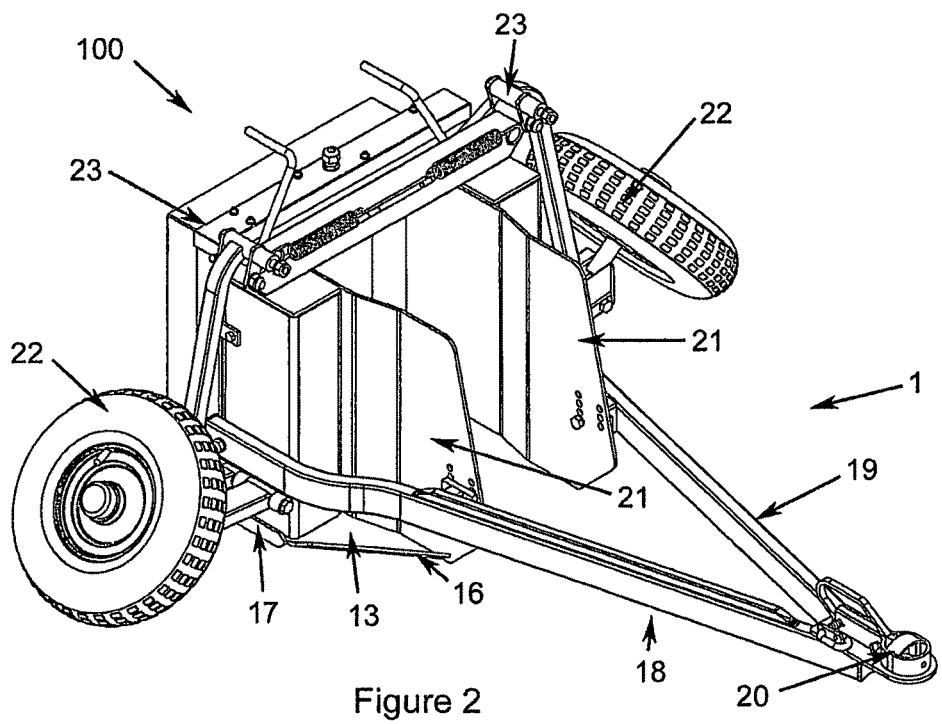
FIG. 2: shows a perspective view of the frame of FIG. 1 with the sensor in the operative position.
Figure 3:
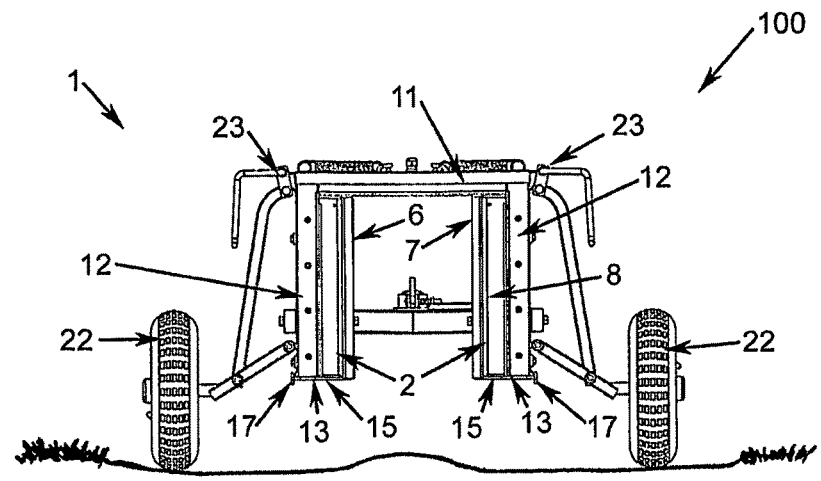
FIG. 3: shows an end elevation of the frame of FIG. 1 in the non-operational, transport configuration.

To facilitate transport of the pasture meter 100 the frame 1 further includes a pair of wheels 22, one adjacent either sensor arm 2. The wheels are pivotable, in an arc substantially vertically perpendicular to their axis of rotation, between a first, transport position, at which the wheels 22 are in ground contact and holding the pasture meter 100 a clearance distance above the ground (as shown in FIGS. 1 and 3) and a second, retracted, position at which the wheels 22 are pivoted up and out of ground contact, allowing the skids 13 of the pasture meter 100 to engage the ground (as shown in FIGS. 2 and 4). A lever arm mechanism 23 is used to actuate the wheels 22 from the first, transport position to the second, retracted, position and vis versa. Preferably once in one or other position the wheels 22 are locked in that position via a locking mechanism (not shown).

When the wheels 22 are in the retracted position they act as outrigger stabilisers, so that if, during operation, the pasture meter 100 hits a large bump or the like and starts to tilt over the corresponding wheel 22 on the down side of the tilt will engage the ground briefly, prevent the meter 100 from tipping over, and encourage it to right itself.

Key advantages of having the pasture sensor operate from the back of a vehicle such as an ATV are that accurate and fast mapping or recording of pasture yields and growth rates are possible. Further, large areas can be covered, including all paddocks accessible by an ATV. With more measurements increased accuracy of result is achieved, and with fast measurement the information obtained can be used at all levels of farm management, including at the operational (day to day grazing), tactical (feed budgeting), and strategic (Zone management, yield mapping, VRT) levels.

The invention further provides a suite of PC based computer software for analysing data received from the pasture meter 100, either by manual transferal of the values for the average weight of dry matter per hectare for each paddock generated by the Pasture meter 100 or, optimally, via electronic means.

At its most basic level, and where an average reading for each paddock is all that is required, that data can be displayed on a display on the console 3, and noted down by the operator.

Optionally and alternatively, data from the pasture sensor console can be uploaded directly to a PDA, either wirelessly, or via a connection cable. From the PDA the data is then downloaded to a PC. Preferably the data transfer module used to transfer the data electronically also allows paddock identifiers and areas to be downloaded from the PC into the PDA, and then into the pasture sensor console, to minimise the amount of data the operator needs to enter in the field so that when initiating the measurement of a paddock all the operator need do would be to either enter a paddock number or select a paddock from a predefined list.

Figure 7:
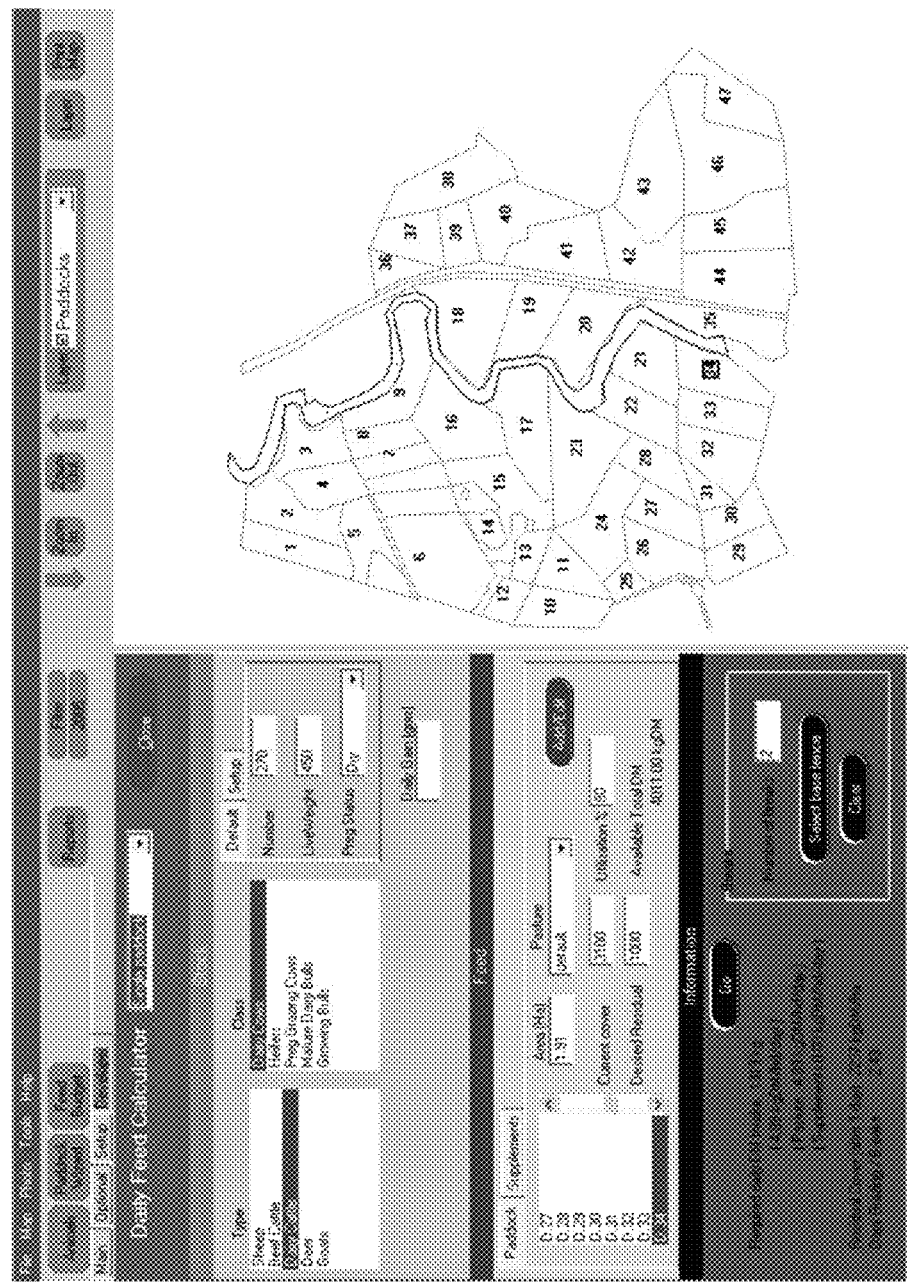
FIG. 7: shows a sample screen shot of the software of the present invention.

Once the data is downloaded to PC the pasture cover module of the software, as exemplified in screen shot illustrated at FIG. 7, then records the average pasture cover by paddock by date, allows that to be modified by choosing different or modifying the pasture equations to reflect different seasons or other environmental considerations, establishes target pasture cover values by paddock by month based on known feed requirements, display existing feed levels in as a paddock feed wedge and, using historical comparative data from earlier pasture sensor readings, together with predetermined seasonal information, pasture type information, and weather information, forecast future feed availability.

As shown in FIG. 7, much of the information can be displayed with reference to a farm GPS map, and can be printed with reference to that map. Further feed break fences and the like can be drawn in by the software using predetermined parameters.

In more preferred embodiments data from the pasture meter console 3 can be uploaded directly to a PDA in real-time or in batches. This allows the operator the flexibility of keeping the PDA in a jacket pocket while riding around the paddock.

Conveniently the uploaded data can be represented in real time on the paddock map displayed on the PDA to produce a readings trail allowing on the fly assessment of the acceptability of the reading process. It also provides an audit trail to show that the operator has complied with correct method of covering the paddock. Once sensing has been completed the uploaded data can then be downloaded from the PDA to the PC based software.

Figure 8:
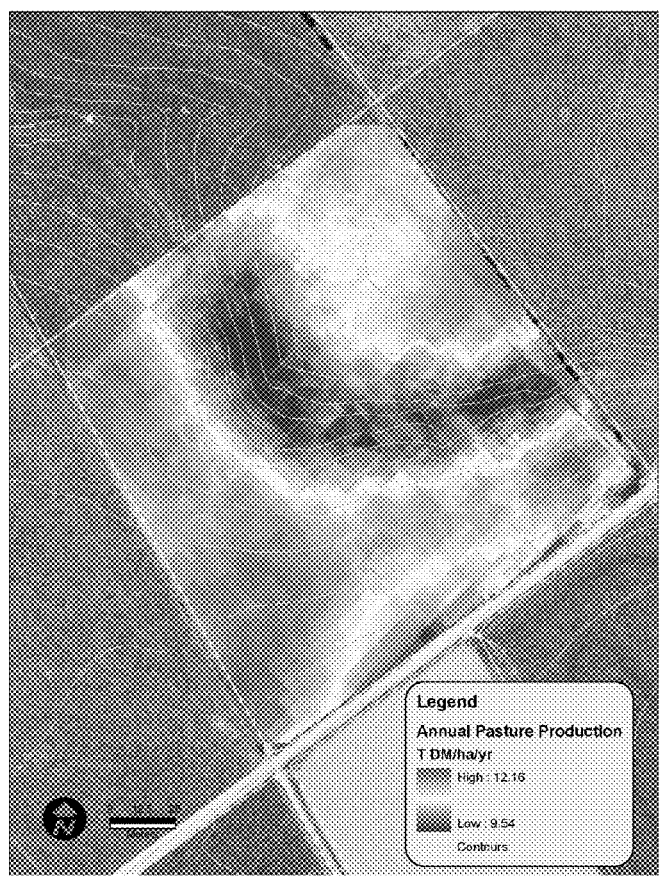
FIG. 8: shows a feed cover map produced by the software of the present invention using readings obtained from the pasture sensor of the present invention.

Preferably where the data available from the pasture sensor is geo-referenced the software can also generate a contoured map of the paddock assessed to show variations in the feed availability within the paddock and enables analysis of the pasture cover in different regions of a paddock, as illustrated in FIG. 8.

The mapping module utilises the Kriging algorithm to display a pasture contour/profile map based on the geo-referenced pasture readings. It also extrapolates feed data to the edges of paddock and displays feed density by reference to colour coded contours and graduations.

Based on the data obtained, a feed forecasting module of the software suite can create lists of available supplement types, and associated volume requirements, forecast available feed versus animal requirements, estimate remaining feed on the farm in days, calculate, show and adjust the number of break fences, calculate grazing rotation up to a week ahead, and create break fences based on pasture density. Data such as preferred minimum cover can be input, and pasture versus animal requirements forecasting undertaken.

The resultant output of this analysis can be downloaded to PDA, including break feed GPS waypoints, and supplements data.

Using optional pasture analysis features of the software suite a comparison of pasture cover data against targets, year to date and prior years figures can be undertaken, as can benchmarking against regional data, and a comparison of growth rates versus weather conditions.

Key production areas within a paddock can be identified and displayed, such as areas of sweet grass, and highly grazed or damaged areas. These can be overlaid with records of fertiliser application, irrigation and drainage layouts. This can then be used to optimise and target specific areas for fertiliser application, optimise feed amounts, and accurately plan soil drainage and irrigation.

Much of this information can also be downloaded to PDA so that relevant information is available in the field where it can be updated and uploaded back to the PC software.

The method and pasture management system of the present invention is illustrated schematically in FIG. 6. It uses the pasture sensor 1 of the invention towed behind an ATV 500 to provide geo-referenced pasture cover data via GPS 200 to the PC based software suite 300 of the invention, thereby enabling optimal and efficient decision making. A PDA 400 can be used to provide in the field access to the resultant information, and as a tool to transfer and update data.

The processing of the data once available from the pasture sensor is essentially as described above with reference to the software. The data flow is as illustrated in FIG. 5. In that regard, and broadly speaking, the method comprising the steps of:

a. Undertaking an initial assessment of the feed availability in one or more paddocks using the pasture sensor of the first broad aspect to secure geo-referenced pasture cover data;

b. Uploading the geo-referenced pasture cover data from the pasture sensor to the software of the third broad aspect above, and determining feed availability variations within each paddock; and c. Referencing the feed availability variations within a paddock optimise the location or locations for break fencing so as to ensure optimised feed availability within the break fenced area as necessary for the number of animals and production considerations applicable.

Preferably the method further includes the steps of uploading the paddock and break fence location data to a PDA to enable the break fencing locations to be established and verified in the field.

Desirably the method further includes the steps of taking subsequent geo-referenced pasture cover readings for the same paddocks after a predetermined time period for subsequent use as indicated in steps b and c, and additionally for comparative assessment with the initial and any subsequent geo-referenced data sets for the same paddock to enable changes in pasture cover to be monitored at any position within the said paddock thereby facilitating location specific decisions to be made as to fertiliser application, watering, drainage, and over sowing, as well as the monitoring and re-assessment of the impact of those decisions to be undertaken.

Referring specifically to FIG. 5, in its most preferred form the data flow involves the pasture meter 100 taking 200 height readings per second. Pasture height is averaged over 1 or a few seconds. The processor in the console 3 on the towing vehicle calculates a KgDM/Ha figure from the height information using a linear equation. It also calculates a rolling average for height. The data is transferred wirelessly to a PDA every few seconds. When each paddock is completed summary data including the average height is also transmitted to the PDA.

An application on the PDA (or the processor in the console 3 of the pasture meter 100) writes shared summary and detail files. If these files were created by the processor they are then transferred to the PDA. Directly on the PDA a software application allows a feed calculation to be performed and additional details recorded.

Once the pasture meter reading process has been completed the PDA is docked with a PC and the shared summary and detail files transferred.

The pasture cover module of the software suite on the PC imports and populates the software suite database with the pasture cover readings.

From the resultant pasture cover tables in the software suite database various processes are undertaken, including:

a. the software suite pasture cover module generates and shows a feed wedge and other data resulting from analysis;

b. pasture cover reports are generated;

c. pasture growth is modelled; and d. the pasture cover is contour mapped and a Kriging analysis undertaken.

Using the software in conjunction with geo-referenced pasture cover data opens the door to a level of strategic analysis previously not possible, and provides an opportunity for significant performance improvements through continuous information feedback versus annual feedback with yield maps.

Figure 9:
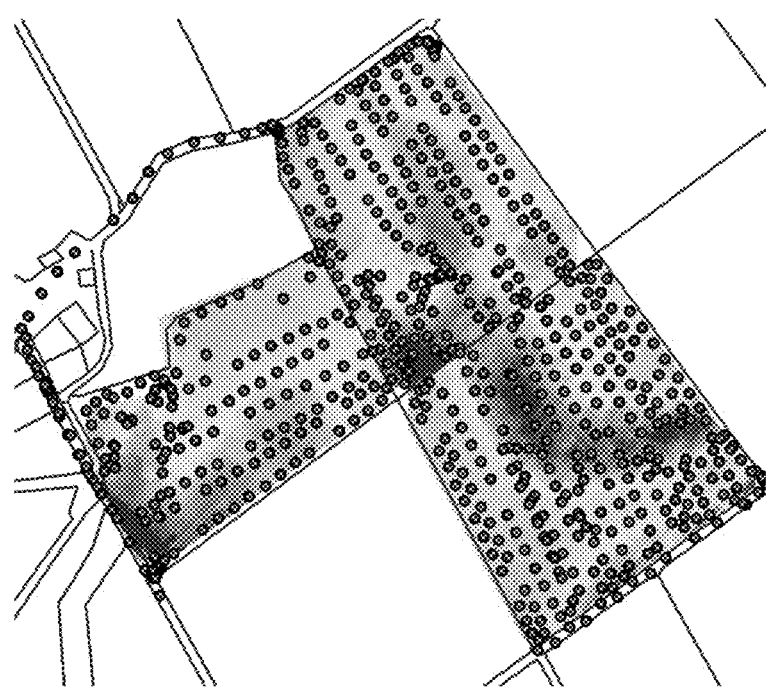
FIG. 9: shows a GPS snail trail of the points at which the pasture sensor of the present invention took pasture sensor readings.

Use of the pasture sensor enables the collection of data at a speed and level of efficiency not previously possible, with the only significant on the ground data collection device until now being a plate meter. Further, use of the pasture sensor reduces variability due to operator technique, and the number of readings produces a more accurate result. Further, with GPS functionality operator performance can be audited based on the data collection "snail trail", as illustrated in FIG. 9.

The display of accurately rendered pasture cover data onto a GPS farm map gives the ability to identify variations in productivity within areas of paddocks, and thereby plan fertiliser application, irrigation and drainage requirements to maximise overall paddock productivity while at the same time avoid wastage of resources through application to areas not requiring those resources.

As noted earlier, by increasing the number of sensors and increasing the reading recordal rate a far more detailed picture amounting to a silhouette of the pasture can be obtained from which it is possible to derive more information. The advantage of having a silhouette which is basically a binary mathematical array of 1's and 0's is that it can be handled and analysed very quickly and efficiently.

Having sufficient data to establish a silhouette of the pasture traversed enables a far greater level of information to be derived about the pasture condition, make up and feed value. Post processing of the gathered data can either take place on the fly as part of the pasture sensor processing functionality, or as part of the software suite.

By comparing the silhouette profile with sample profiles the software can determine qualitative characteristics of the pasture. Whether this is done on the fly by the pasture sensor console, or via the PC software, analysing the silhouette profile enables the determination of the actual plant type and the percentage of that plant growing along the path traversed through the paddock.

This in turn can lead to far more accurate determination of the feed content in the paddock by the percentage of the various plant types growing in it e.g. grasses, weeds etc.

Traditionally pasture cover has been measured in kilograms of dry matter per hectare. However a more useful measurement is of the metabolisable energy, measured in mega joules, of the pasture. Several factors influence the conversion ratio from kilograms of dry matter per hectare to mega joules of energy. This includes the pasture grass type, the season, recent weather conditions, and whether the grass is short and lush, or long and stalky, and the presence of weeds.

Automatically applying the appropriate metabolisable energy value for each particular plant time as it appears in the silhouette, or even undertaking that calculation on a measured pasture content basis would provide a more accurate measure in mega joules of the available feed value.

Using this approach would negate the need to select from pre-defined dry matter to available feed formulae, which currently requires operator involvement to select the correct formula for the time of year.

Using silhouette imaging analysis can be supplemented by inputting pasture type reference information for each paddock to provide a base line or, alternatively the software could take the latitude and long coordinates from the GPS point and couple that with the date to automatically reference the correct formula for that time and region.

Another advantage that flows from the silhouette analysis approach is the ability to detecting things like urine spots in paddocks. These can be later utilised for variable rate fertiliser application, by cutting down the fertiliser application in area where there is a high density of urine spots.

The method can also used to identify patches of weeds which could then be sprayed out. Patches of thistle can be easily detected for example. Further, the degree of variation over a short distance will also give an indication of quality. For example pugged areas will be more variable in pasture cover, with very uneven or sparse stands of grass.

The method and systems of the present invention provide both immediate and long term benefits. The short term benefits include more accurate placing of break fences and calculation of the amount of supplementary feed required.

This means the cows are less likely to be underfed (detrimental to production) or overfed (which is wasteful).

The long term benefits centre around identifying areas or zones within a paddock that are less productive than others (or have less palatable grass). This means that application of fertilisers, weed sprays, drainage, irrigation, over sowing of pasture etc can be targeted at particular zones within a paddock.

Also with the level of information available through use of the system and method of the invention the effect of different grazing regimes can be quantified. This allows the farmer to experiment with different techniques in terms of the initial and residual cover—for example in any given area is it best to graze a paddock lightly or hard? This allows the farmer to optimise grazing rotations specifically to their individual farm (as opposed to using text book or traditional approaches). Traditionally only research organisations would have had the ability to quantify the effect of different pasture management approaches to down to this level of detail.

Additional advantages of the present invention will become apparent to those skilled in the art after considering the principles in particular form as discussed and illustrated.

Accordingly it will be appreciated that changes may be made to the above described embodiment of the invention without departing from the principles taught herein. For example, where in the foregoing description reference has been made to integers or components having known equivalents then such equivalents are herein incorporated as if individually set forth.

Other uses for the pasture sensor, with minimal modification, are expressly contemplated, such as measuring crop growth and yield, field production performance, vine and tree growth and in similar applications.

Finally it will be understood that the invention is not limited to the particular embodiment described or illustrated, but is intended to cover all alterations or modifications which are within the scope of the invention as claimed.

The invention claimed is:

1. A sensor assembly comprising:
   a) a sensor comprising:
      i. a pair of parallel spaced apart substantially vertically disposed sensor arms;
      ii. a plurality of emitters spaced along the length of a first of said arms, each emitter configured and arranged to, in use, emit a signal towards a second of said arms substantially perpendicularly to the said first of said arms; and
      iii. a plurality of receivers spaced along the length of the second of said arms, the receivers being configured and arranged to, in use, receive signals emitted by the emitters;
   b) a controller configured to, in use, control the emission of signals by each of the said emitters;
   c) a data collector configured to, in use, collect data from each receiver as to the existence or absence of receipt of a signal,
   d) a processor to process data received from the controller and the data collector and to determine the height of any plant matter traversed by the sensor at predetermined intervals, and
   e) memory to store the plant matter height data generated by the processor for subsequent download or analysis;
   f) a support frame configured to support the sensor in a substantially vertical orientation and configured for attachment to a towing vehicle;
   g) a pair of spaced apart deflector guards configured and arranged to, in use, present a defined bandwidth of pasture passing between the sensor arms, the defined bandwidth of pasture being narrower than the space between the sensor arms; and
   h) ground engagement means configured to maintain the support frame and the sensor at a predetermined level above the ground during operation.

2. The sensor according to claim 1 wherein each emitter is optimised to emit a high intensity pulse of infra-red light and each receiver is optimised to receive said high intensity pulse of infra-red light.

3. The sensor according to claim 2 wherein the sensor includes twelve emitters paired with twelve receivers and wherein the emitters operate as four banks of three, with every fourth emitter along the length of the first sensor arm being part of the same bank.

4. The sensor according to claim 3 wherein each bank of emitters emits a pulse of infra-red light in series, preferably with each bank emitting a pulse of no more than 100 milliseconds long.

5. The sensor according to claim 1 wherein the sensor is adapted to be able to take at least 200 readings per second.

6. The sensor according to claim 1 wherein the processor monitors the receivers for faults, so that if a potential fault is detected the console is able to provide an alert to an operator.

7. The sensor according to claim 1 further including a GPS receiver such that, in use, each set of data collected by the collector is geo-referenced as to its collection position.

8. The sensor according to claim 1 configured and arranged as a pasture sensor to determine pasture density as kilograms of dry matter per hectare.

9. The sensor according to claim 8 wherein the control console further includes a user input interface to enable an operator to input the appropriate time of year and pasture type so that the processor uses appropriate conversion calculations when calculating pasture density.

10. The sensor according to claim 8 wherein the number of pairs of emitters and receivers and the sensor reading rate is sufficient to generate a constant silhouette of the plant matter along the line of sensor travel.

11. The sensor according to claim 10 wherein the processor is adapted to automatically determine the pasture type based on real-time analysis of the silhouette by the processor.

12. The sensor according to claim 11 wherein the processor is adapted to determine in real-time an appropriate metabolised energy value for each particular plant in the silhouette on the basis of recognition via the silhouette.

13. The sensor according to claim 1 further including wireless data transfer means to wirelessly upload and download data.

14. The sensor assembly according to claim 1 wherein the ground engagement means comprise a pair of parallel spaced apart skids wherein each skid further includes a downwardly projecting blade running substantially the length of the underside of said skid.

15. The sensor assembly according to claim 1 further including wheels for transporting the sensor from one location to another while not in use, the wheels being arranged such that the ground engagement means are not in ground engagement during said transporting.

16. The sensor assembly according to claim 15 wherein the transport wheels are adapted to move from a transport position to a second position whereat the ground engagement means are in ground engagement and said transport wheels serve as stabilizers against the support frame tipping over sideways, when at said second position.

17. A sensor assembly according to claim 1 wherein the defined bandwidth of pasture is 20-200 millimeters narrower than the space between the sensor arms.

18. A sensor assembly comprising:
 a) a sensor comprising:
  i. a pair of parallel spaced apart substantially vertically disposed sensor arms;
  ii. a plurality of emitters spaced along the length of a first of said arms, each emitter configured and arranged to, in use, emit a signal towards a second of said arms substantially perpendicularly to the said first of said arms; and
  iii. a plurality of receivers spaced along the length of the second of said arms, the receivers being configured and arranged to, in use, receive signals emitted by the emitters;
 b) a support frame and two or more skids, skis or wheels mounted to the support frame and configured to ride on the ground during operation, the support frame and skids, skis or wheels being configured to support the sensor with each of said arms in a substantially vertical orientation and to maintain the sensor at a fixed predetermined level above the ground during operation, and the support frame being configured for attachment to a towing vehicle;
 c) a pair of spaced apart deflector guards configured and arranged to, in use, present a defined bandwidth of pasture passing between the sensor arms, the defined bandwidth of pasture being narrower than the space between the sensor arms;
 d) a data collector configured to, in use, collect data from each receiver as to the existence or absence of receipt of a signal;
 e) memory to store the collected data for subsequent download or analysis; and
 f) a processor for analyzing the collected data to determine pasture cover.

19. The sensor assembly according to claim 18 configured and arranged so as to be sufficiently heavy that, in use, the ground beneath the skids is slightly flattened as the skids pass over thereby achieving a smoother ride.

20. The sensor assembly according to claim 19 adapted to be towed at a rate of 15-25 kph.

21. A method of gathering crop or pasture data, using a sensor assembly comprising:
 a) a sensor comprising:
  i. a pair of parallel spaced apart substantially vertically disposed sensor arms;
  ii. a plurality of emitters spaced along the length of a first of said arms, each emitter configured and arranged to, in use, emit a signal towards a second of said arms substantially perpendicularly to the said first of said arms; and
  iii. a plurality of receivers spaced along the length of the second of said arms, the receivers being configured and arranged to, in use, receive signals emitted by the emitters;
 b) a support frame and two or more skids, skis or wheels mounted to the support frame and configured to ride on the ground during operation, the support frame and skids, skis or wheels being configured to support the sensor with each of said arms in a substantially vertical orientation and to maintain the sensor at a fixed predetermined level above the ground during operation, and the support frame being configured for attachment to a towing vehicle;
 c) a pair of spaced apart deflector guards configured and arranged to, in use, present a defined bandwidth of pasture passing between the sensor arms, the defined bandwidth of pasture being narrower than the space between the sensor arms;
 d) a data collector configured to, in use, collect data from each receiver as to the existence or absence of receipt of a signal; and
 e) memory to store the collected data for subsequent download or analysis;
the method comprising the steps of:
towing the sensor assembly over pasture using the towing vehicle;
the data collector collecting data from the receivers;
storing the collected data in the memory; and
determining a pasture cover or pasture density based on the collected data.

* * * * *